United States Patent [19]

Kaiser et al.

[11] Patent Number: 4,585,662
[45] Date of Patent: * Apr. 29, 1986

[54] ACYCLIC ALCOHOL ODORANT AND/OR FLAVORING SUBSTANCES

[75] Inventors: Roman Kaiser, Uster; Dietmar Lamparsky, Wangen, both of Switzerland

[73] Assignee: Givaudan Corporation, Clifton, N.J.

[*] Notice: The portion of the term of this patent subsequent to Feb. 25, 2003 has been disclaimed.

[21] Appl. No.: 624,090

[22] Filed: Jun. 25, 1984

Related U.S. Application Data

[62] Division of Ser. No. 283,774, Jul. 16, 1981, Pat. No. 4,482,762.

[30] Foreign Application Priority Data

Jul. 31, 1980 [CH] Switzerland ............ 5839/80
Jun. 17, 1981 [CH] Switzerland ............ 3996/81

[51] Int. Cl.$^4$ .................. A23L 2/26; A61K 7/46
[52] U.S. Cl. ................... 426/534; 131/276; 252/174.11; 252/522 R; 424/49; 424/69; 424/70; 424/76
[58] Field of Search .......... 252/522 R, 174.11; 131/276; 426/534; 424/49, 69, 70, 76

[56] References Cited

U.S. PATENT DOCUMENTS

| | | | |
|---|---|---|---|
| 3,781,368 | 12/1973 | Neale | 568/687 X |
| 3,859,366 | 1/1975 | Schleppnik | 252/522 R X |
| 4,006,109 | 2/1977 | Ochsner et al. | 252/522 R |
| 4,168,248 | 9/1979 | Kulka | 252/522 R |
| 4,347,388 | 8/1982 | Gramlich et al. | 252/522 R X |

OTHER PUBLICATIONS

Arctander, *Perfume and Flavor Chemicals*, vol. II, Monographs 1960 and 1961 (1969).
Bjelouss, Ber., vol. 43, p. 233 (1910).

*Primary Examiner*—Thomas A. Waltz
*Attorney, Agent, or Firm*—Robert F. Tavares

[57] ABSTRACT

The invention is concerned with compounds of the formula:

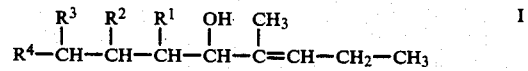

$$R^4-CH-CH-CH-CH-C=CH-CH_2-CH_3$$
with substituents $R^3, R^2, R^1, OH, CH_3$ on successive carbons     I wherein one of the symbols $R^1, R^2$ and $R^3$ stands for methyl or ethyl and the others stand for hydrogen and $R^4$ signifies hydrogen or methyl, with the proviso that $R^4$ represents hydrogen when $R^1$ and $R^2$ both represent hydrogen and $R^3$ represents methyl and their use as odorants and flavorants.

7 Claims, No Drawings

ACYCLIC ALCOHOL ODORANT AND/OR FLAVORING SUBSTANCES

This is a division of application Ser. No. 283,774 filed July 16, 1981, now U.S. Pat. No. 4,482,762.

The invention is concerned with novel odorant and/or flavouring substances.

The novel odorant and/or flavouring substances provided by the invention are compounds of the formula

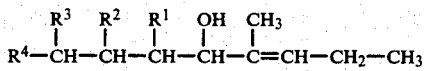

wherein one of the symbols $R^1$, $R^2$ and $R^3$ stands for methyl or ethyl and the others stand for hydrogen and $R^4$ signifies hydrogen or methyl, with the proviso that $R^4$ represents hydrogen when $R^1$ and $R^2$ both represent hydrogen and $R^3$ represents methyl.

Formula I is accordingly intended to embrace the secondary $C_{10-12}$-alcohols:
3,6-Dimethyl-6-nonen-5-ol [Ia],
4-methyl-3-decen-5-ol [Ib],
4,6-dimethyl-3-nonen-5-ol [Ic],
4-methyl-3-nonen-5-ol [Id],
4,7-dimethyl-3-octen-5-ol [Ie],
4,6-dimethyl-3-octen-5-ol [If],
4-methyl-6-ethyl-3-octen-5-ol [Ig],
4-methyl-6-ethyl-3-nonen-5-ol [Ih],
4-methyl-7-ethyl-3-nonen-5-ol [Ij] and
4,8-dimethyl-3-decen-4-ol [Ik],
in the form of their two possible stereoisomers (cis- or trans-configuration at the double bond).

The invention is also concerned with a process for the manufacture of the compounds of formula I.

DESCRIPTION OF THE PREFERRED EMBODIMENTS

This process comprises reacting 2-methyl-2-pentenal with a compound of the formula

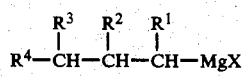

wherein $R^1$ to $R^4$ have the above significance and X stands for halogen.

The halide of formula II can be any halide, but the bromide is preferably used.

The reaction of methylpentenal with a compound of formula II is conveniently carried out according to methods which are known per se for carrying out Grignard reactions; see, for example, Organikum, Org. chem. Grundpraktikum, reprint 15th Edition, VEB deutscher Verlag der Wissenschaften, Berlin 1977, 617 et seq. Thus, the reaction is conveniently carried out in diethyl ether as the solvent and at a temperature of about 0°–35° C.

According to the process provided by the invention, the compounds of formula I are obtained in the form of an isomer mixture in which the trans-form predominates to a large extent.

On economical grounds this isomer mixture is preferably used.

The compounds of formula I have particular organoleptic properties, on the basis of which they are excellently suited as odorant and/or flavouring substances.

The invention is therefore also concerned with the use of the compounds of formula I as odorant and/or flavouring substances.

The 3,6-dimethyl-6-nonen-5-ol [Ia], for example, has a flowery, fruity and at the same time green odour with a warm undertone, whereby powdery nuances reminiscent of chocolate can be established in the bottom note, whereas the 4-methyl-3-decen-5-ol [Ib] has above all fruity and very natural odour notes, whereby especially in the initial smell there appears a note which is pleasantly fresh-green and at the same time reminiscent of violets. In the case of both compounds there is a reminiscence, inter alia, of green notes which can also be observed in the case of marguerites and tagetes. Hitherto, these notes could be realised by a single substance only with difficulty. The tagetone and tagetenone which are known, for example, as the constituent of tagetes are, moreover, as the conjugated unsaturated ketones very unstable. It is to be noted that, for example, no rose-like odour appears and not only the compound Ia but also the compound Ib are very clearly removed in their total odour emission from known compounds of similar structure.

In general, it has been found that the alcohols of formula I with 11 carbon atoms have a green-fruity note with accentuation of the fruity character, whereas the corresponding alcohols with only 10 carbon atoms (Id-If) have practically no fruity character, but are distinguished by intensive fresh-green odour notes without flowery sidenotes.

On the basis of their natural odour notes the compounds of formula I are especially suitable for the modification, for example, (α) known flowery compositions in which, for example, the citrus notes are to be emphasised (e.g. for cologne types and the like, essences), (β) known fruity compositions for example, of the raspberry type ("extrait" types, compositions of the feminine direction), (γ) known tobacco and woody compositions ("extrait" types of the masculine direction) and finally (δ) known compositions having green notes in which, in particular, a desired rounding-off and harmonising effect are produced.

Very interesting effects are produced odour-wise when the compound of formula Ia and/or Ib is used together with the known 2,6-dimethyl-6-nonen-5-ol (III), namely the compound of the formula

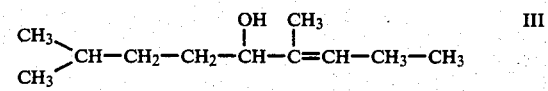

whereby the ratio of the compound of formula Ia and/or Ib to the compound of formula III can vary in a wide range; for example, the ratio can lie between 1% of compound of formula Ia and/or Ib and 99% of compound of formula III (or vice versa).

In order to prepare the mixtures, the compound of formula Ia and/or Ib and the compound of formula III are admixed, or the starting material of formula II used in the process provided by the invention can contain optional amounts of iso-amylmagnesium halide.

The extraordinary diffusion of the odorant substance compositions produced by means of the above mixtures is especially noteworthy. However, increased freshness and naturalness are also noticeable.

In this connection, it is surprising that the compound of formula III alone does not have any organoleptic interest. Thus, this compound is described, for example, by Bjelouss, in Ber. 43, 233 (1910) as of flat odour. Experiments carried out in the scope of the present invention have also confirmed that the compound of formula III has, indeed, an extremely weak and insignificant odour of its own. Also, the determination of the threshold value confirms that the compounds of formula I are strong odorant substances and the compound of formula III is a weak odorant substance.

The compounds of formula I combine with numerous known natural or synthetic ingredients of odorant and/or flavouring substance compositions, whereby the range of the natural ingredients can embrace not only readily-volatile but also semi-volatile and difficultly-volatile substances, and the range of the synthetic ingredients can embrace representatives from almost all classes of substances, as will be evident from the following compilation:

Natural products: Basil oil, tree moss absolute, mugwort oil, bergamot oil, cassis bud absolute, castoreum, cedarwood oil, Cistus labdanum, civet, coriander oil, oak moss, elemi oil, pine-needle oil, galbanum, geranium oil, jasmine absolute and its synthetic substitute, jonquille absolute, labdanum, lavender oil, mandarin oil, mastix absolute, palmarosa oil, patchouli oil, petitgrain oil Paraguay, sandalwood oil, thyme oil, frankincense, ylangylang oil, lemon oil etc.

Alcohols: Citronellol, geraniol, cis-3-hexenol, linalool, phenylethyl alcohol, rhodinol, Sandela® (3-isocamphyl-5-cyclohexanol) etc.

Aldehydes: α-Amylcinnamaldehyde, cyclamen aldehyde, dodecanal, heliotropin, α-hexylcinnamaldehyde, hydroxycitronellal, 2,6,10-trimethyl-undec-9-en-1-al (Adoxal™), undecanal, ω-undecylene aldehyde etc.

Ketones: Isoraldeine® (isomethyl-α-ionone), α-ionone, β-ionone, 3-prenylisocaranone, Vertofix™ (acetylated cedarwood oil) etc.

Esters: Amyl salicylate, benzyl acetate, citronellyl acetate, cis-3-hexenyl acetate, cis-3-hexenyl benzoate, 1-methyl-2-secbutylcyclohexyl acetate, methyl dihydrojasmonate, phenoxyethyl isobutyrate, phenylethyl tiglate, styrallyl acetate, 2,3,6,6-tetramethylcyclohex-2-ene carboxylic acid ethyl ester, 3,6,6-trimethyl-2-ethylcyclohexy-2-ene carboxylic acid ethyl ester, vetivenyl acetate etc.

Various: Coumarin, eugenol, isobutylquinoline, limonene, p-methane-8-thiol-3-one, 1-methylcyclododecyl methyl ether, γ-nonalactone, γ-undecalactone, musk ambrette, Galaxolid™ (1,3,4,6,7,8-hexahydro-4,6,6,7,8,8-hexa-methyl-cyclopenta-γ-2-benzopyran), musk ketone, Musk 174™ (12-oxahexadecanolid) etc.

The compounds of formula I or mixtures of compounds of formula I with the compound of formula III can be used in wide limits which, for example, can range in compositions from 0.1% in the case of detergents to 50% in the case of alcoholic solutions. It will be appreciated that these values are not limiting values, since the experienced perfumer can also produce effects with still lower concentrations or can synthesize novel complexes with still higher concentrations (e.g. with up to 40%). The preferred concentrations vary between 0.5% and 20%. The compositions produced with compounds of formula I or mixtures of the compounds of formula I with the compound of formula III can be used for all kinds of perfumed consumer goods (Eau de Cologne, eau de toilette, "extraits" (essences), lotions, creams, shampoos, soaps, salves, powders, toothpastes, mouth washes, deodorants, detergents, tobacco etc).

The compounds of formula I or the mixtures of compounds of formula I with the compound of formula III can accordingly be used for the production of odorant compositions and, as will be evident from the foregoing compilation, using a wide range of known odorant substances. In the production of such compositions the known odorant substances specified earlier can be used according to methods which are known to the perfumer such as, for example, according to W. A. Poucher, Perfumes, Cosmetics and Soaps 2, 7th Edition, Chapman and Hall, London, 1974.

As flavouring substances, the compounds of formula I can be used, for example, for the production, improvement, intensification, enhancement or modification of fruit flavours (e.g. melon, peach, apricot), of berry flavours, especially raspberry flavours, or of chocolate flavours (Ia+III) in foodstuffs (yoghurt, sweet goods etc), in luxury consumables (tea, tobacco etc) and drinks (lemonades etc).

The pronounced flavour qualities of the compounds of formula I enable them to be used in low concentrations. A suitable concentration lies, for example, within the range of 0.01–100 ppm, preferably 0.1–20 ppm, in the finished product (i.e. the flavoured foodstuff, luxury consumable or drink).

In the flavouring of, for example, tobacco the concentration can, however, also be higher and can extend over a wider range, for example the range of 1–1000 ppm, preferably 50–500 ppm.

The compounds can be mixed with the ingredients used for flavouring substance compositions or added to such flavourants in the usual manner. Among the flavourants contemplated in accordance with the invention there are to be understood flavouring substance compositions which can be diluted or dispersed in edible materials in a manner known per se. They contain, for example, about 0.1–10 weight %, especially 0.5–3 weight %. They can be converted according to methods known per se into the customary forms of use such as solutions, pastes or powders. The products can be spray-dried, vacuum-dried or lyophilised.

The known flavouring substances which are conveniently used in the production of such flavourants are either already referred to in the foregoing compilation or can be readily selected from the literature such as, for example, from J. Merory, Food Flavourings, Composition, Manufacture and Use, Second Edition, The Avi Publishing Company Inc., Westport, Conn. 1968, or from G. Fenaroli, Fenaroli's Handbook of Flavour Ingredients, Second Edition, Volume 2, CRC Press Inc., Cleaveland, Ohio, 1975.

For the manufacture of such customary forms of use there can be used, for example, the following carrier materials, thickening agents, flavour-improvers, spices, auxiliary ingredients etc:

Gum arabic, tragacanth, salts or brewers' yeast, alginates, carrageen or similar absorbants; indoles, maltol, dienals, spice oleoresins, smoke flavours; cloves, diacetal, sodium citrate; monosodium glutamate, disodium inosine-5'-monophosphate (IMP), disodium guanosine-5-phosphate (GMP); or special flavouring substances, water, ethanol, propyleneglycol, glycerine.

The following Examples illustrate the present invention:

EXAMPLE 1

3,6-Dimethyl-6-nonen-5-ol (Ia)

0.72 g (29.8 mg atoms) of magnesium in 3 ml of absolute ether are placed in an apparatus which is customary for Grignard reactions. While stirring there are subsequently added dropwise 5.0 g (33.1 mmol) of 1-bromo-2-methylbutane (90%) in 5 ml of absolute ether so that the ether boils constantly. After completing the addition of the bromide, the mixture is held at reflux temperature for a further 30 minutes, then cooled to 10° C. and a solution of 2.92 g (29.8 mmol) of 2-methyl-2-pentenal in 3 ml of absolute ether is added dropwise. The exothermic reaction causes the temperature to rise to 25° C. After refluxing for a further hour, the reaction product is worked-up with crushed ice and saturated ammonium chloride solution in the customary manner. After separating the aqueous phase, the organic layer is washed with saturated sodium chloride solution, subsequently dried and freed from solvent. The crude product (4.8 g) is distilled and yields 1.74 g of pure 3,6-dimethyl-6-nonen-5-ol (boiling point about 120° C./12 mm Hg; $n_D^{20}=1.4560$), which has the following spectral data:

IR (liq. film): 3350, 2960, 2928, 2876, 1670, 1462, 1378, 1004, 856 cm$^{-1}$.

NMR (360 MHz): 0.88+0.89 (d+t, 6H), 0.965 (t, 3H); 1.59 (s, 3H); 2.015 (m, 2H), 4.08 (m, 1H); 5.38 (t, 1H).

MS (70 eV): m/e=170(3), 155(2), 141(12), 99(78), 81(27), 71(23), 55(28), 43(100).

EXAMPLE 2

4-Methyl-3-decen-5-ol (Ib)

2.4 g (0.1 g atom) of magnesium in 50 ml of absolute ether are placed in an apparatus which is customary for Grignard reactions. While stirring and under a protective gas atmosphere (nitrogen) there are subsequently added dropwise 15.0 g (0.1 mol) of n-amyl bromide in 50 ml of absolute ether so that, after initiation of the reaction, the ether constantly boils slightly. After completing the addition, the mixture is held at reflux temperature for a further 30 minutes, then cooled to 10° C. and a solution of 7.85 g (0.08 mol) of 2-methyl-2-pentenal in 20 ml of absolute ether is added dropwise. In order to complete the reaction, the mixture is stirred at room temperature for a further 12 hours. After decomposing the Grignard complex with saturated ammonium chloride solution and ice, the supernatant ethereal solution is washed with saturated sodium chloride solution and subsequently dried. After evaporating the solvent, there remain 13.6 g of crude product which are fractionally distilled. There are thus obtained 8.9 g of pure 4-methyl-3-decen-5-ol of boiling point 103° C./12 mm Hg, $n_D^{20}=1.4499$.

SPECTRAL DATA

IR: 3340, 2958+2924, 2888+1858, 1670, 1460, 1024 854 cm$^{-1}$.

NMR (360 MHz): 0.89 (t,3H); 0.965 (t, 3H); 1.595 (s,3H); 2.03 (m, 2H); 3.96 (t, 1H), 5.36 (t, 3H).

MS: m/e=170 (M+, 6), 155(1), 141(18), 128(2), 109(2) 99(100), 81(19), 71(15), 55(19), 43(42).

EXAMPLE 3

2,6-Dimethyl-6-nonen-5-ol ((III)+small amount of Ib)

69.5 g (2.9 g atoms) of magnesium are placed in 500 ml of absolute ether. Subsequently, a solution of 438 g of isoamyl bromide, which contains ca 1.5% n-amyl bromide in accordance with gas chromatography, in 1.2 l of absolute ether is added dropwise so that the exothermic reaction maintains the ether constantly at the boiling point. After completing the addition, the mixture is held at reflux temperature for a further 30 minutes. The Grignard solution is thereupon cooled to 10° C. Then, 236.5 g (2.41 mol) of 2-methyl-2-pentenal in 600 ml of absolute ether are added dropwise within 40 minutes, the temperature being held between 10° and 20° C. during the addition. In order to complete the reaction, the mixture is held at reflux temperature for a further 1 hour. The mixture is subsequently added to ice, decomposed with aqueous hydrochloric acid, the ethereal solution is washed neutral with sodium carbonate solution and saturated sodium chloride solution and then dried. The crude product (480 g) remaining after distillation of the solvent is fractionally distilled over a Widmer column and gives 312 g of 2,6-dimethyl-6-nonen-5-ol (III) of boiling point 62° C./0.05 mm Hg; $n_D^{25}=1.4479$, which contains 1.5% of 4-methyl-3-decen-5-ol in accordance with gas chromatography (Carbowax, 130° C.).

SPECTRAL DATA (III)

IR: 3350, 2956+2930, 2866, 1670, 1468, 1386, 1368, 1012, 856 cm$^{-1}$.

NMR (60 MHz): 0.88+0.90 (converging, 9H); 1.59 (s, 3H); 2.02 (t, 2H); 3.93 (t, 1H); 5.33 (t, 1H).

MS: m/e=170(7), 141(16), 123(4), 99(100), 81(34), 71(19), 55(36), 43(91).

EXAMPLE 4

1:1 Mixture of 2,6-dimethyl-6-nonen-5-ol (III) with 4-methyl-3-decen-5-ol (Ib)

In a manner analogous to Examples 1 to 3 there is added dropwise to 1.6 g of magnesium in 20 ml of absolute ether a solution of a mixture of 5.0 g of n-amyl bromide and 5.0 g of isoamyl bromide in 40 ml of absolute ether so that the ether boils constantly. After completing the addition, the mixture is left to react at the reflux temperature of the ether for a further 30 minutes and is then worked-up as described in Examples 1-3. There are obtained 8.4 g of crude product, which, after distillation in vacuo, yield 7.7 g of a mixture, which, in accordance with gas chromatography, contains 54% of 2,6-dimethyl-6-nonen-5-ol and 46% of 4-methyl-3-decen-5-ol (boiling point of the mixture 97°-100° C./12 mm Hg).

EXAMPLE 5

4,6-Dimethyl-3-nonen-5-ol 28.3 g (1.18 g atoms) of magnesium in 200 ml of ether are placed in an apparatus which is customary for Grignard reactions. While stirring and under a protective gas atmosphere (nitrogen) there are subsequently added dropwise 178.1 g (1.18 mol) of 2-bromopentane in 500 ml of absolute ether so that, after initiation of the reaction, the ether constantly boils slightly. After completing the addition, the mixture is held at reflux temperature for a further 30 minutes, then cooled to 10° C. and a solution of 96.1 g (0.98 mol) of 2-methyl-2-pentenal in 300 ml of ether is added dropwise during 30 minutes so that the reaction temperature during the addition lies between 10° and 20° C. In order to complete the reaction, the mixture is refluxed for 1 hour, then the Grignard complex is decomposed with saturated ammonium chloride solution and ice, the supernatant ethereal solution is washed with saturated sodium chloride solution and subsequently dried. After evaporating the solvent, there remain behind 176 g of crude product, which are fractionally distilled. There are thus obtained 119 g (71.4%) of olfactorily good 4,6-dimethyl-3-nonen-5-ol of boiling point 92° C./12 mm Hg.

SPECTRAL DATA

IR: 3380, 2958, 2924, 2865, 1670, 1460, 1378, 1300, 1005, 854.

NMR: 0.70–1.20 (2t and 1d, mutually overlapping, 9H); 1.58 (s, 3H), 2.02 (m, 2H); 3.67 (m, 1H); 5.34 (t, J~6.5, 1H).

MS: 170 (M+, 2), 141(2), 128(3), 123(1), 109(1), 99(100), 81(25), 71(12), 55(11), 43(72).

Odour: green (privet), fruity-spicy, fatty, cocoa-like.

EXAMPLE 6

4-Methyl-3-nonen-5-ol

A Grignard reagent [29.1 g (1.2 g atoms) of magnesium in 300 ml of ether and 164 g (1.2 mol) of butyl bromide in 500 ml of ether] is reacted with 98.15 g (1 mol) of 2-methyl-2-pentenal in 200 ml of ether in a manner analogous to Example 5. Fractional distillation of the crude product (195.2 g) over a 20 cm Widmer column gives 124.2 g (79.5%) of olfactorily good 4-methyl-3-nonen-5-ol of boiling point 89°–90° C./12 mm Hg.

SPECTRAL DATA

IR: 3350, 3958, 3925, 2870, 2858, 1670, 1460, 1380, 1305, 1110, 1050, 1002, 885.

NMR: 0.80–1.20 (2t, 6H); 1.60 (s, 3H); 2.02 (m, 2H); 3.98 (t, J~6.5, 1H); 5.36 (t, J~6.5, 1H).

MS: 156 (M+, 2), 127(8), 114(2), 99(36), 81(16), 71(12), 57(12), 55(16), 43(100), 41,25).

Odour: fatty, green, diffuse ("montant").

EXAMPLE 7

4,7-Dimethyl-3-octen-5-ol

A Grignard reagent, prepared by reacting 11.8 g (0.49 g atom) of magnesium in 50 ml of ether and 67.13 g (0.49 mol) of isobutyl bromide in 250 ml of ether, is reacted with 40.0 g (0.41 mol) of 2-methyl-2-pentenal in 100 ml of ether in a manner analogous to Example 5. Fractional distillation of the crude product (94 g) over a 20 cm Widmer column give 44.4 g (69.4%) of olfactorily good 4,7-dimethyl-3-octen-5-ol of boiling point 47°–48° C./0.04 mm Hg.

SPECTRAL DATA

IR: 3350, 2958, 2930, 2865, 1670, 1468, 1383, 1367, 1305, 1050, 1000, 856.

NMR: 0.80–1.20 (1d+1t, 9H); 1.60 (s, 3H); 2.02 (m, 2H); 4.08 (t, J~6.5, 1H); 5.37 (t, J~6.5, 1H).

MS: 156 (M+, 9); 127(24), 114(16), 109(6), 99(100), 81(32), 71(26), 55(19), 43(80), 41(43).

Odour: green with earthy-musty side-note.

EXAMPLE 8

4,6-Dimethyl-3-octen-5-ol

A Gringnard reagent, prepared by reacting 18.7 g (0.77 g atom) of magnesium in 100 ml of ether and 105.4 g (0.77 mol) of 2-bromobutane in 300 ml of ether, is reacted with 62.72 g (0.64 mol) of 2-methyl-2-pentenal in 200 ml of ether in a manner analogous to Example 5. Fractional distillation of the crude product (98.8 g) over a 20 cm Widmer column gives 68.4 g (68.5%) of olfactorily good 4,6-dimethyl-3-octen-5-ol of boiling point 83° C./12 mm Hg.

SPECTRAL DATA

IR: 3400, 2960, 2930, 2870, 1670, 1460, 1378, 1300, 1035, 1000, 858.

NMR: 0.70–1.10 (2t+1d, mutually overlapping, 9H); 1.58 (s, 3H); 2.02 (m, 2H); 3.68 (m, 1H); 5.37 (t, J~6.5, 1H).

MS: 156 (M+, 1), 109(1), 99(54), 81(20), 71(10), 57(12), 55(15), 43(100), 41(22), 39(7).

Odour: fresh, green, herb-like.

EXAMPLE 9

4-Methyl-6-ethyl-3-octen-5-ol

A Grignard reagent, prepared by reacting 29.4 g (1.21 g atoms) of magnesium in 200 ml of ether and 183 g (1.21 mol) of 3-bromopentane in 400 ml of ether, is reacted with 98.0 g (1.0 mol) of 2-methyl-2-pentenal in a manner analogous to Example 5. Fractional distillation of the crude product (159.3 g) over a 20 cm Widmer column gives 95.5 g (56.2%) of olfactorily good 4-methyl-6-ethyl-3-octen-5-ol of melting point 92°–93° C./12 mm Hg.

SPECTRAL DATA

IR: 3400, 2960, 2930, 2870, 1670, 1460, 1378, 1300, 1040, 1010, 910, 855.

NMR: 0.70–1.10 (3t, mutually overlapping, 9H); 1.60 (s, 3H); 2.08 (m, 2H); 3.80 (m, 1H); 5.33 (t, J~6.5, 1H).

MS: 170 (M+, 1) 141(0.5); 99(71), 81(24); 71(18); 57(12), 55(22), 43(100), 41(28).

Odour: fruity, cocoa-like aspect of maraschino.

EXAMPLE 10

4-Methyl-7-ethyl-3-nonen-5-ol

A Grignard reagent, prepared by reacting 11.4 g (0.47 g atom) of magnesium in 100 ml of ether and 77.6 g (0.47 mol) of 1-bromo-2-ethylbutane in 400 ml of ether, is reacted with 38.4 g (0.39 mol) of 2-methyl-2-pentenal in a manner analogous to Example 5. Fractional distillation of the crude product (79.8 g) over a 15 cm Widmer column gives 29.9 g (40.3%) of olfactorily good 4-methyl-7-ethyl-3-nonen-5-ol of boiling point 105°–106° C./12 mm Hg.

SPECTRAL DATA

IR: 3350, 2955, 2920, 2865, 1670, 1460, 1378, 1300, 1002, 853.

NMR: 0.70–1.10 (3t, mutually overlapping, 9H); 1.60 (s, 3H); 2.05 (m, 2H); 4.10 (m, 1H); 5.38 (t, J~6.5, 1H).

Odour: fruity, green, flowery.

In the following formulation Examples A stands for a mixture of 98% of III, 1.5% of Ib and 0.5% of Ia.

EXAMPLE 11

Perfumery base in the direction of modern cologne

| | Parts by weight |
|---|---|
| 2-Ethyl-3,6,6-trimethyl-2-cyclohexene-1-carboxylic acid ethyl ester (Myrascone TM) | 80 |
| 1,3,4,6,7,8-Hexahydro-4,6,6,7,8,8-hexamethylcyclopenta-δ-2-benzopyran (Galaxolide TM) | 60 |
| Hydroxycitronellal | |
| 1-Methyl-1-methoxycyclododecane (Madrox TM) | 60 |

-continued

| | Parts by weight |
|---|---|
| 3-Isocamphyl-5-cyclohexanol (SANDELA ®) | 60 |
| Bergamot oil | 60 |
| Pine-needle oil | 30 |
| Musk ketone | 40 |
| 2-Ethyl-6,6-dimethyl-2-cyclohexene-1-carboxylic acid ethyl ester (Givescone ™) | 20 |
| 3-Prenyl-isocaranone | 20 |
| Petitgrain oil Paraguay | 15 |
| p-Menthane-8-thiol-3-one | 5 |
| Tree Moss absolute | 5 |
| Propyleneglycol | 450 |
| | 965 |

An addition of 35 parts of the novel mixture A brings to this cologne very much more life and more volume; the composition becomes stronger, fruity-spicy and at the same time markedly delightful and enchanting.

EXAMPLE 12

Perfumery base in the direction of Calèche ®

| | Parts by weight |
|---|---|
| Hydroxyciteonellal | 250 |
| Vetivenyl acetate | 100 |
| Bergamot oil | 100 |
| 3-Isocamphyl-5-cyclohexanol (SANDELA ®) | 100 |
| Phenylethyl alcohol | 60 |
| Isomethyl-α-ionone (ISORALDEINE ®) | 100 |
| Jasmine (synthetic) | 50 |
| Rhodinol | 50 |
| Musk ketone | 30 |
| Ylang oil | 20 |
| Dodecanal (10% in DPG) | 20 |
| Coumarin | 10 |
| Undecanal (10% in DPG) | 10 |
| Dipropyleneglycol (DPG) | 80 |
| | 950 |

The addition of 50 parts by weight of the novel mixture A to the foregoing composition brings about a greater softness in its top note and produces a pleasant fruity-flowery nuancing.

EXAMPLE 13

Perfumery base in the direction of Cabochard ®

| | Parts by weight |
|---|---|
| Isoraldeine ® | 200 |
| Musk ambrette | 100 |
| Phenylethyl alcohol | 100 |
| Bergamot oil | 100 |
| Tree moss | 50 |
| Vetivenyl acetate | 50 |
| Jasmine (synthetic) | 50 |
| Patchouli oil | 40 |
| Rhodinol | 40 |
| Eugenol | 40 |
| 3-Isocamphyl-5-cyclohexanol (SANDELA ®) | 40 |
| α-Hexylcinnamaldehyde | 40 |
| 1-Methyl-1-methoxycyclododecane (Madrox ™) | 30 |
| Civet synthetic (10% in dipropyleneglycol [DPG]) | 20 |
| Styrallyl acetate | 20 |
| Castoreum (synthetic) | 2 |
| Isobutylquinoline (10% in DPG) | 10 |
| Hydrocycitronellal | 50 |
| Undecylene aldehyde (10% in DPG) | 10 |
| Lemon oil | 5 |
| γ-Undecalactone | 2 |
| Labdanum resinoid | 1 |

-continued

| | Parts by weight |
|---|---|
| | 1000 |

If 100 parts by weight of the novel mixture A are added to the foregoing composition, then the novel composition through its flowery-fruity tendency becomes very much more interesting and clearly has more diffusion. In the bottom there comes into play a greater sweetness, which substantially improves the somewhat dry bottom note of the original composition.

EXAMPLE 14

Perfumery base in a green-flowery direction

| | Parts by weight |
|---|---|
| Hydroxycitronellal | 250 |
| Methyl dihydrojasmonate | 250 |
| Propyleneglycol | 200 |
| Bergamot oil | 100 |
| Citronellol | 50 |
| p-Menthane-8-thio-3-one (1°/∞) | 10 |
| Mandarine oil | 10 |
| Galbanum oil | 10 |
| Jasmine (synthetic) | 10 |
| Palmarosa oil | 10 |
| Mastix absolute | 5 |
| Geranium oil Bourbon | 5 |
| Cyclamen aldehyde | 5 |
| Coriander oil | 5 |
| Phenoxyethyl isobutyrate | 5 |
| Cis-3-hexenol (10% in propyleneglycol) | 5 |
| Basil oil | 3 |
| Cassis bud oil (absolute) | 2 |
| | 935 |

If 65 parts of the novel compound Ia are added to the foregoing green-flowery base, then the muguet note and lilac note appear much clearer. After the addition of the compound Ia, the composition becomes extremely harmonic.

EXAMPLE 15

Perfumery composition in the direction of fougère

| | Parts by weight |
|---|---|
| Lavender oil | 210 |
| Amyl salicylate | 200 |
| Tree moss absolute (50% in dipropyleneglycol) | 100 |
| Citronellol | 100 |
| Geraniol | 80 |
| Musk ambrette | 80 |
| Bergamot oil | 80 |
| α-Ionone | 80 |
| α-Amylcinnamaldehyde | 25 |
| Eugenol | 20 |
| 1-Acetoxy-1-methyl-2-sec.butylcyclohexane | 25 |
| | 1000 |

If 20% of the novel mixture A are added to the foregoing base, then the lavender note is suppressed, while the violet head note becomes a very interesting novel fougère element. The bottom becomes very much sweeter and more flowery.

EXAMPLE 16

Perfumery composition in the direction of chypre

| | Parts by weight |
|---|---|
| 1-Methyl-1-methoxycyclododecane (Madrox ™) | 200 |
| Bergamot oil | 150 |
| Hydroxycitronellal | 100 |
| Citronellol | 80 |
| Petitgrain oil | 60 |
| 12-Oxahexadecanolide (Musk 174 ™) | 60 |
| Coriander oil | 40 |
| Galbanum oil | 40 |
| Cedarwood oil | 40 |
| Patchouli oil | 40 |
| Lemon oil | 40 |
| Elemi oil | 10 |
| Oak moss | 25 |
| Pine-needle oil Pumillon | 110 |
| | 995 |

If 15 parts by weight of the novel compound Ib are added to the foregoing base, then the citrus-bergamotte note is underlined very advantageously. The galbanum note now becomes "pleasantly clothed".

EXAMPLE 17

Perfumery composition having a general flowery note

| | Parts by weight |
|---|---|
| Dipropyleneglycol | 200 |
| Limonene | 150 |
| α-Ionone | 60 |
| Citronellol | 50 |
| Linalool | 50 |
| Acetylated Cedarwood oil (Vertofix ™) | 50 |
| 1,3,4,6,7,8-Hexahydro-4,6,6,7,8,8-hexamethylcyclopenta-δ-2-benzopyran (Galaxolide ™) | 50 |
| Benzyl acetate | 30 |
| 2-Ethyl-3,6,6-trimethyl-2-cyclohexene-1-carboxylic acid ethyl ester (Myrascone ™) | 30 |
| Jasmine (synthetic) | 20 |
| Musk ketone | 20 |
| Phenylethyl tiglate | 20 |
| Frankincense (50% in propylene glycol) | 15 |
| Citronellyl acetate | 10 |
| Cis-3-hexenyl acetate (10% in propyleneglycol) | 10 |
| Ylang oil | 10 |
| Ylang (synthetic) | 10 |
| Lemon oil | 15 |
| 2,2,8-Trimethyl-7-nonen-3-ol | 15 |
| γ-Undecalactone | 5 |
| Cyclamen aldehyde | 5 |
| Galbanum | 5 |
| Sandalwood oil | 5 |
| Jonquille absolute (10% in propyleneglycol) | 5 |
| Cistus labdanum oil | 5 |
| 2,6,10-Trimethyl-9-undecen-1-al (Adoxal ™) (10% in propylenecol) | 5 |
| | 830 |

If 170 parts of the novel compound Ia are added to the foregoing flowery base, a pronounced "cosmetic effect" results in the novel composition, which now becomes simultaneously much more diffuse, fresher and charming.

EXAMPLE 18

Perfumery base in the direction of gardenia

| | Parts by weight |
|---|---|
| Hydroxycitronellal | 150 |
| Bergamot oil | 140 |
| α-Ionone | 100 |
| α-Amyl-cinnamaldehyde | 85 |
| Heliotropin | 80 |
| Styrallyl acetate | 80 |
| Ylang-ylang oil | 80 |
| Benzyl acetate | 80 |
| Phenylethyl alcohol | 80 |
| Linalool | 80 |
| γ-Nonalactone (10% in dipropyleneglycol) | 20 |
| Jasmine (synthetic) | 15 |
| γ-Undecalactone (10% in dipropyleneglycol) | 10 |
| | 1000 |

The addition of 15% of the novel mixture A to the foregoing basic composition brings out its top note substantially fuller. There is observed a clearly increased diffusion with a simultaneous change from sharp gardenia to a slight violet-like, soft-flowery odour, which is very well suited for cosmetics.

EXAMPLE 19

| Fruity base | Parts by weight |
|---|---|
| Limonene | 500 |
| Linalool | 200 |
| Cis-3-hexenyl benzoate | 60 |
| Benzyl acetate | 40 |
| Citronellol | 30 |
| 2,2,8-Trimethyl-7-nonen-3-ol | 30 |
| Cis-3-hexenyl acetate (10% in DGP) | 20 |
| Phenylethyl tiglate | 20 |
| γ-Undecalactone | 10 |
| Citronellyl acetate | 10 |
| | 920 |

The addition of 80 parts by weight of the novel mixture A to the foregoing composition leads to an extremely interesting enrichment of the citrus fruit note; the novel composition becomes less hard, without the individual odour of the novel compound coming through.

We claim:

1. An odorant and/or flavoring composition comprising an olfactory effective amount of a compound of the formula:

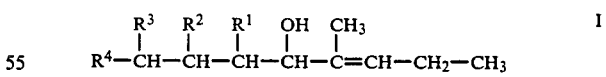

wherein:
(i) one of the symbols $R^1, R^2$ and $R^3$ stands for methyl or ethyl and the others stand for hydrogen, and
(ii) $R^4$ signifies hydrogen or methyl, with the proviso that $R^4$ represents hydrogen when $R^1$ and $R^2$ both represent hydrogen and $R^3$ represents methyl and at least one other olfactory agent.

2. A composition according to claim 1 wherein the compound is 3,6-dimethyl-6-nonen-5-ol or 4-methyl-3-decen-5-ol.

3. An odorant and/or flavoring composition comprising 2,6-dimethyl-6-nonen-5-ol in admixture with 3,6- dimethyl-6-nonen-5-ol and/or 4-methyl-3-decen-5-ol and at least one other olfactory agent.

4. A method for improving the olfactory properties of odorant and/or flavor compositions which comprises adding thereto an effective amount of a compound of the formula:

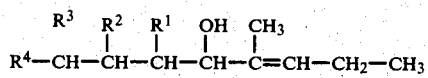

wherein:

(i) one of the symbols $R^1$, $R^2$ and $R^3$ stands for methyl or ethyl and the others stand for hydrogen, and (ii) $R^4$ signifies hydrogen or methyl, with the proviso that $R^4$ represents hydrogen when $R^1$ and $R^2$ both represent hydrogen and $R^3$ represents methyl.

5. A method according to claim 4 wherein the compound added is 3,6-dimethyl-6-nonen-5-ol or 4-methyl-3-decen-5-ol.

6. A method according to claim 5 wherein 3,6-dimethyl-6-nonen-5-ol and/or 4-methyl-3-decen-5-ol is added together with 2,6-dimethyl-6-nonen-5-ol.

7. A composition comprising 2,6-dimethyl-6-nonen-5-ol in admixture with 3,6-dimethyl-6-nonen-5-ol and/or 4-methyl-3-decen-5-ol.

* * * * *

UNITED STATES PATENT AND TRADEMARK OFFICE
CERTIFICATE OF CORRECTION

PATENT NO. : 4,585,662
DATED : April 29, 1986
INVENTOR(S) : Roman Kaiser et al.

It is certified that error appears in the above-identified patent and that said Letters Patent is hereby corrected as shown below:

On the Title page, [*] Notice, correct "The portion of the term of this patent subsequent to February 25, 2003 has been disclaimed." to read --The portion of the term of this patent subsequent to November 13, 2001 has been disclaimed.--.

In claim 4, column 13, line 13, correct the structure

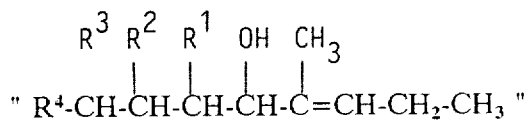

to read

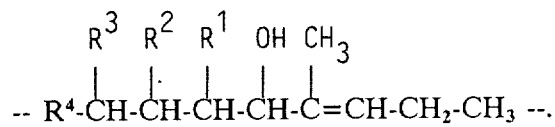

UNITED STATES PATENT AND TRADEMARK OFFICE
CERTIFICATE OF CORRECTION

PATENT NO. : 4,585,662

DATED : April 29, 1986

INVENTOR(S) : Roman Kaiser et al.

It is certified that error appears in the above-identified patent and that said Letters Patent is hereby corrected as shown below:

In claim 6, column 14, line 9, correct "claim 5" to read --claim 4--.

Signed and Sealed this

Seventh Day of August, 1990

*Attest:*

HARRY F. MANBECK, JR.

*Attesting Officer*     *Commissioner of Patents and Trademarks*